United States Patent [19]

Kobayashi et al.

[11] Patent Number: 5,013,323
[45] Date of Patent: May 7, 1991

[54] IMPLANT MATERIAL FOR REPLACING HARD TISSUE OF LIVING BODY

[75] Inventors: Masahiro Kobayashi, Funabashi; Hideo Tagai, Ota; Yoshikatsu Kuroki, Yokohama; Shigeo Niwa, Aza; Mikiya Ono, Hanno, all of Japan

[73] Assignee: Mitsubishi Mining & Cement Co., Ltd., Tokyo, Japan

[21] Appl. No.: 86,247

[22] Filed: Aug. 13, 1987

Related U.S. Application Data

[63] Continuation of Ser. No. 799,755, Nov. 19, 1985, abandoned.

[30] Foreign Application Priority Data

Dec. 4, 1984 [JP] Japan ................................ 59-255006

[51] Int. Cl.$^5$ ................................................ A61F 2/28
[52] U.S. Cl. ............................................ 623/16; 501/1
[58] Field of Search ............... 623/16, 66; 501/1, 35, 501/95

[56] References Cited

U.S. PATENT DOCUMENTS

| | | | |
|---|---|---|---|
| 3,597,249 | 8/1971 | Shannon | 501/35 X |
| 3,861,927 | 1/1975 | Kimura et al. | 501/58 X |
| 4,017,322 | 4/1977 | Kawai et al. | 427/443.2 X |
| 4,131,597 | 12/1978 | Blüethgen et al. | 623/16 X |
| 4,222,128 | 9/1980 | Tomonaga et al. | 623/16 |
| 4,471,019 | 9/1984 | Wegerhoff et al. | 428/224 |
| 4,655,777 | 4/1987 | Dunn et al. | 623/16 |

*Primary Examiner*—Alan Cannon
*Attorney, Agent, or Firm*—Jordan and Hamburg

[57] ABSTRACT

An implant material for replacing hard tissue of a living body is provided. The implant material comprises 10 to 90 wt % of a fiber glass and 90 to 10 wt % of an organic high polymer material. The fiber glass is mainly composed of calcium phosphate. The organic high polymer material does not inhibit affinity with the living body. On the surface of the implant material, a portion of the fiber glass is exposed.

23 Claims, No Drawings

IMPLANT MATERIAL FOR REPLACING HARD TISSUE OF LIVING BODY

This application is a continuation of application Ser. No. 799,755, filed Nov. 19, 1985, now abandoned.

BACKGROUND OF THE INVENTION

The present invention relates to an implant material for replacing hard tissue of a living body, and more particularly to novel implant material for replacing a defect or hollow portion of hard tissue, such as bone or dental root, resulting from external injury or surgical removal of bone tumor.

In surgical and orthopedic treatments, prosthesis operations are often required for filling in defects or hollow portions of bone resulting from fracture of bone or surgical removal of bone tumor. Also in the field of dental surgery, similar denture operations are often required for filling in spoilt void portions in maxilla or mandibula resulting from pyorrhea alveolaris. It has been a common practice to resect ilium or other bone tissue from the patient to fill up the defect or hollow portion of bone thereby to promote early remedy of the bone tissue. However, by means of such an operation, normal bone tissue must be picked up from an unspoilt portion which causes additional pain to the patient and in addition the operation is very troublesome. Moreover, when the volume of defect or void in the patient's bone is large, the amount of bone obtainable from his own body is not always sufficient for fully filling in the defect or void. In such a case, it is inevitable to use a substitute for the patient's own bone tissue.

A variety of metal alloys and organic materials have hitherto been used as the substitute for hard tissue in the living body. However, it has been recognized that these materials tend to dissolve or otherwise deteriorate in the environment of living tissue or to be toxic to the living body, and that they cause a so-called foreign body reaction. Ceramic materials are used up to date, since they are excellent in compatibility with living body and are free of the aforementioned difficulties. From ceramic materials, particularly alumina, carbon or tricalcium phosphate or a sintered mass or single crystal of hydroxyapatite, which are superior in compatibility with living body, artificial bones and tooth roots have been developed and have attracted a good deal of public attention.

However, the conventional ceramic implant materials have a common disadvantage in that they are inherently too hard and brittle, and in that they are difficultly machined to have a shape and dimensions adapted to be filled in the void of bone. On the other hand, when alumina is used as the filler, it acts as a stimulant to cause absorption of bone at the vicinity of the implanted filler, since alumina is much harder than the bone tissue. The use of ceramic materials or alumina has not yet been in the stage of practical application, accordingly.

The hard tissues of living body have, in general, a density of about 1.9 g/cm$^3$, a bending strength of from 300 to 1800 kg/cm$^2$ and a modulus of bending elasticity of $1.6 \times 10^5$ kg/cm$^2$. It is thus desired that the implant material has a bending strength and a modulus of bending elasticity comparable to those of the hard tissues of living body, as set forth above, and a density substantially equivalent to or less than that of the hard tissues of living body, and that it can be easily machined to have a shape and dimensions well adapted to be fitted in a void into which it is implanted. It is further desired that the implant material does not hinder the affinity with the living body but it promotes positively the formation of new bone.

SUMMARY OF THE INVENTION

A primary object of this invention is to provide an implant material for replacing hard tissue of a living body, which is excellent in affinity or compatibility with the living body and has a mechanical strength substantially equivalent to or higher than that of the hard tissue of the living body, the mechanical strength thereof being adjustable, and has an excellent machineability to be shaped to have a desired contour and dimensions.

Another object of this invention is to provide an implant material for replacing hard tissue of a living body, which promotes formation of new bone when implanted in a living body.

A further object of this invention is to provide an implant material for replacing hard tissue of a living body, which is superior in toughness.

A still further object of this invention is to provide an implant material for replacing hard tissue of a living body, which does not cause the loosening problem.

The above and other objects of this invention will become apparent from the following detailed description of the invention.

According to the invention, there is provided an implant material for replacing hard tissue of a living body, comprising 10 to 90% by weight of a fiber glass mainly composed of calcium phosphate and 90 to 10% by weight of an organic high polymer material not inhibiting affinity with the living body, a portion of the fiber glass being exposed on the surface of the implant material.

DETAILED DESCRIPTION OF THE PREFERRED EMBODIMENTS

The present invention will now be described in detail.

It is preferred that the fiber glass mainly composed of calcium phosphate contains a total content of CaO and P$_2$O$_5$ of not less than 15% by weight, and has a molar ratio of Ca/P of from 0.3 to 4.0. If the total content of CaO and P$_2$O$_5$ is less than 15% by weight, the affinity with living body deteriorates, thus delaying recovery of bone tissue. On the other hand, if the molar ratio of Ca/P is less than 0.3, the viscosity of a feed molten mass becomes so low as to make it difficult to form fibers therefrom. On the contrary, if the molar ratio of Ca/P is more than 4.0, it becomes impossible to melt the glass or the viscosity of the molten mass becomes too high to spin fibers therefrom. Even if fibers might be spun from a glass having a molar ratio of Ca/P of more than 4.0, the fibers become opaque due to devitrification and are too weak to be applied for practical use. The fiber glass used in the present invention may contain, other than CaO and P$_2$O$_5$, other inorganic ingredients which are not harmful to the living body. Examples of such inorganic ingredients include Al$_2$O$_3$, SiO$_2$, Na$_2$O, K$_2$O, MgO and Fe$_2$O$_3$.

As the sources of calcium and phosphorous for the fiber glass mainly composed of calcium phosphate, according to the invention, a calcium phosphate compound such as tetracalciumphosphate, hydroxyapatite, tricalcium phosphate or animal bones may be used. The aforementioned calcium phosphate compounds may be combined with other phosphorous-containing compounds, such as triammonium phosphate, ammonium hydrogenphosphate, sodium phosphate, phosphoric acid or mixtures thereof, or may be combined with other calcium-containing compounds, such as quick lime, slaked lime, calcium carbonate or mixtures thereof. Alternatively, the other phosphorous-containing compounds and the other calcium-containing compounds may be used in combination in lieu of the calcium phosphate compounds. If necessary, the starting material may be mixed with one or a mixture of two or more of inorganic oxides selected from alumina, silica, sodium oxide, potassium oxide, iron oxide, magnesium oxide, potash feldspar and kaolin. The animal bones or kaolin of natural resources may be contained in the starting material for the fiber glass of the invention, as described before, as far as they do not contain harmful contaminants for the living body, such as arsenic or cadmium, or contain only a trace amount of such a harmful contaminant.

The fiber glass mainly composed of calcium phosphate, according to the present invention, may be prepared by the steps of mixing the aforementioned starting materials to form a material mixture, putting the material mixture into a crucible provided with a nozzle at the bottom thereof, melting the mixture at about 800° C. to 1700° C. to allow the molten mixture to discharge from the nozzle, and blowing a high pressure gas onto the discharged flow of molten mixture, whereby staple fibers are formed. Alternatively, fibers of long filament form may be formed by continuously taking up the spun filaments discharged through the nozzle around a drum or roller.

The fiber glass mainly composed of calcium phosphate, according to the invention, may be combined with an organic polymer material which does not inhibit affinity with the living body, in the form of staple fiber or long filament without any further treatment. However, it may be woven to form a woven cloth or gauze which may be combined with the organic polymer material. The woven cloth or gauze made of the fiber glass of the invention may be prepared using a commercially available manually or automatically operated weaving machine.

It is preferred that the surface of the fiber glass mainly composed of calcium phosphate, according to the present invention, be coated with or have deposited thereon a calcium phosphate compound. The compatibility with living body of the fiber glass mainly composed of calcium phosphate can be further improved to facilitate growth of new bone and to accelerate repair and recovery of the living bone structure integrally unified with the filled fiber glass, if the surface of each fiber glass mainly composed of calcium phosphate is coated with a calcium phosphate compound.

The surface of each glass fiber mainly composed of calcium phosphate may be coated with or have deposited thereon a calcium phosphate compound by dipping the glass fibers mainly composed of calcium phosphate in a solution containing phosphoric ions, such as a solution of ammonium hydrogenphosphate or a mixed solution of phosphoric acid and ammonia, to allow the phosphoric ions present in the solution to react with calcium ions in the glass fibers to form a calcium phosphate compound over the surface of each fiber. According to this process, the calcium phosphate compound deposited on the surface of each fiber has a molar ratio of Ca/P of from 0.8 to 1.7. Alternatively, a slurry of a calcium phosphate compound having a molar ratio of Ca/P of from 1.0 to 2.0 is prepared, and the glass fibers of the invention are dipped in the slurry to allow the calcium phosphate compound to adhere on the surface of each fiber followed by drying.

In the process of depositing a calcium phosphate compound on the surface of each fiber using a solution containing phosphoric ions, the solution may preferably have a pH value of 2 to 7. If the pH value of the solution is less than 2, the fiber glass mainly composed of calcium phosphate deteriorates so as to have a strength weaker than that required for practical use. On the contrary, if the pH value of the used solution is higher than 7, the amount of calcium phosphate compound depositing on the surface of each fiber mainly composed of calcium phosphate becomes too small to reform and improve the surface.

A cloth or gauze may be woven from the reformed fibers of long filament form having the calcium phosphate compound on the surfaces thereof, or a cloth or gauze may be initially woven from fibers of long filament form and then the woven cloth or gauze is subjected to the aforementioned reformation treatment. Alternatively, the fiber glass may be subjected to surface reforming treatment after they are combined with an organic high polymer material.

The organic high polymer material which may be used in the present invention should not inhibit the affinity with the living body. Examples of organic high polymer materials used in the invention include carboxylic acid base polymers, such as polylactic acid and polyglycolic acid; carboxylic ester base polymers, such as polymethylmethacrylate and poly(trifluoroethylmethacrylate); and olefinic polymers, such as polyethylene and polypropylene. Polymethylmethacrylate and poly(trifluoroethylmethacrylate) are the most preferred, since they have high strength and excellent compatibility with the fiber glass mainly composed of calcium phosphate.

According to the present invention, 10 to 90% by weight of the fiber glass mainly composed of calcium phosphate is combined with 90 to 10% by weight of the organic high polymer material not inhibiting affinity with the living body to form a composite material. The composite material may be prepared through an immersion, injection or extrusion process. In the immersion process, a predetermined amount of fiber glass is immersed in a solution of a selected organic high polymer material containing the monomer thereof under a reduced pressure to impregnate the fiber glass with the organic high polymer, and then the polymer material is cured. In the injection process, the fiber glass is preset in a mold into which a hot molten organic high polymer material is injected from an injection cylinder to be combined together. In the extrusion process, a selected organic high polymer material and a fiber glass are heated in an extruder and then extruded through the die of the extruder.

The improved mechanical strength, i.e. excellent bending strength and modulus of bending elasticity, of the implant material is attributed to the fiber glass, whereas the organic polymer material serves as a binder and gives toughness and machineability to the resultant product. If the content of the fiber glass is less than 10% by weight, the mechanical strength of the implant material is lowered. On the contrary, if the content of fiber glass is more than 90% by weight with attendant decrease in content of organic high polymer, a unified composite material cannot be formed or the toughness and machineability of the composite material become unsatisfactory even if a unified composite material is formed.

It is essential that the implant material for replacing hard tissue of a living body, according to the invention, has a portion of the fiber glass being exposed on the surface thereof. Without the fiber glass exposed on the surface of the implant material, the implant material loses the affinity with a living body and the ability for accelerating formation of new bone. It is thus necessary to expose a portion of the fiber glass on the surface of the implant material by rubbing or by removing the organic polymer material using a solvent if the implant material has no such portion.

The bending strength of the implant material of the invention may be adjusted by varying the content of the fiber glass, for example, within the range of from not less than 500 kg/cm² to the maximum value of about 16500 kg/cm². The maximum bending strength is higher by more than 8 times as that of the dense femur of human body. The modulus of bending elasticity of the implant material may be set to a value substantially equal to or slightly higher than that of the dense femur of human body, namely may be set to a value of from $0.6 \times 10^5$ kg/cm² to $5.5 \times 10^5$ kg/cm². The density of the implant material may be set to a value substantially equivalent to that of the dense femur of human body, namely may be set to a value of from 1.3 to 2.3 g/cm³. The implant material of the invention is tough and may be easily cut, shaved or otherwise machined to have a shape snugly fitted in the implanted site.

EXAMPLES OF THE INVENTION

The present invention will now be described more specifically with reference to preferred embodiments thereof. However, it is noted that the following examples are given by way of example only and the invention is not limited only to the following examples but defined by the broad scope of the appended claims.

EXAMPLE 1

Hydroxyapatite ($Ca_5(PO_4)_3OH$), kaolin ($Al_2Si_2O_5(OH)_4$) and potash feldspar ($KAlSi_2O_3$) were pulverized and mixed together, and then the mixture was melted in a crucible at 1100° C. and discharged from a nozzle at the bottom of the crucible to spin a fiber glass containing CaO and $P_2O_5$ in an amount of $CaO + P_2O_5$ of 45% by weight and having a molar ratio of Ca/P of 1.67 and a diameter of 10 to 20 microns. The fiber glasses were combined with each of the organic high polymer materials set forth in Table 1 through an injection process to prepare implant materials of the invention (Diameter: 1.5 cm, Height: 10 cm).

Each of the thus prepared implant materials had a portion of fiber glass exposed on the surface thereof.

Irrespective of the organic polymer materials used in preparation of the composite materials, each implant material containing 10 wt % of fiber had a density of about 1.3 g/cm³, and each implant material containing 90 wt % of fiber had a density of about 2.3 g/cm³. The bending strength and the modulus of bending elasticity of each composite material are shown in Table 1.

TABLE 1

|  | Organic Polymer | \multicolumn{5}{c}{Content of Fiber Glass (wt %)} |
|---|---|---|---|---|---|---|
|  |  | 10 | 30 | 50 | 70 | 90 |
| Bending Strength (kg/cm²) | PMMA (Type D) | 1600 | 3200 | 4900 | 9500 | 16300 |
|  | PMMA (Type F) | 1600 | 3300 | 5100 | 9800 | 16300 |
|  | PMMA (Type H) | 1600 | 3500 | 5000 | 10200 | 16500 |
|  | PTFEMA | 1400 | 2800 | 3900 | 6000 | 8800 |
| Modulus of Bending Elasticity (kg/cm²) | PMMA (Type D) | $1.6 \times 10^5$ | $1.8 \times 10^5$ | $2.0 \times 10^5$ | $3.9 \times 10^5$ | $5.5 \times 10^5$ |
|  | PMMA (Type F) | $1.6 \times 10^5$ | $1.8 \times 10^5$ | $2.0 \times 10^5$ | $3.9 \times 10^5$ | $5.5 \times 10^5$ |
|  | PMMA (Type H) | $1.6 \times 10^5$ | $1.8 \times 10^5$ | $2.0 \times 10^5$ | $3.9 \times 10^5$ | $5.5 \times 10^5$ |
|  | PTFEMA | $1.2 \times 10^5$ | $1.6 \times 10^5$ | $1.8 \times 10^5$ | $3.7 \times 10^5$ | $5.0 \times 10^5$ |

Note:
PMMA: Polymethylmethacrylate available from Mitsubishi Rayon Company Limited. Types D. F. H indicate the specified types selected from commercial designations of M. D. F. V and H of the products of Mitsubishi Rayon Company Limited.
PTFEMA: Poly(trifluoroethylmethacrylate)
Bending Strength: Measured by the JIS R-1601 method.
Modulus of Bending Elasticity: Calculated from the bending strength.

All of the thus prepared implant materials were tough and could be cut by a knife.

EXAMPLE 2

Each of the implant materials prepared by Example 1 and having a fiber glass content of 50% by weight (Diameter: 1.5 cm, Height: 10 cm) was implanted in a musculi dorsi and a diaphysis of femur of a rabbit, and the cellular histochemical reactions were observed through an optical microscope after the lapse of three weeks.

The results revealed that no irritation was caused by any of the implant materials embedded in the musculi dorsi and that a new bone was formed by the implantation in the diaphysis of femur.

EXAMPLE 3

Starting materials as set forth in Table 2 were mixed together, followed by melting at a temperature, respectively, set forth in Table 2 to discharge the molten mass from the bottom of a crucible while blowing with a high pressure air, whereby fiber glass having diameters ranging within 10 to 50 microns were prepared.

TABLE 2

| Run No. | Molar Ratio of Ca/P | $CaO + P_2O_5$ (wt %) | Starting Materials | Melting Temp. (°C.) | Remarks |
|---|---|---|---|---|---|
| 1 | 0.2 | 50 | $Ca_2P_2O_7$, $NH_4H_2PO_4$, $Na_2O$, $SiO_2$ | 680 | Hard to form fibers. |
| 2 | 0.3 | 90 | $Ca_2P_2O_7$, $NH_4H_2PO_4$, $Na_2O$, $SiO_2$ | 800 |  |
| 3 | 2.2 | 50 | $Ca_3(PO_4)_2$, $CaCO_3$, $Al_2O_3$, $SiO_2$, $K_2O$ | 1150 |  |
| 4 | 3.0 | 15 | $CaHPO_4$, $Ca(OH)_2$, $MgO$, $Al_2O_3$, $Fe_2O_3$ | 1400 |  |
| 5 | 4.0 | 50 | $Ca_3(PO_4)_2$, $CaO$, $MgO$, $SiO_2$, $Fe_2O_3$ | 1700 |  |

TABLE 2-continued

| Run No. | Molar Ratio of Ca/P | CaO + P$_2$O$_5$ (wt %) | Starting Materials | Melting Temp. (°C.) | Remarks |
|---|---|---|---|---|---|
| 6 | 4.5 | 80 | CaCO$_3$, (NH$_4$)$_2$HPO$_4$, Al$_2$O$_3$, Fe$_2$O$_3$ | above 1700 | Impossible to form fibers |

50 wt % of each of Run Nos. 2 and 3 of the fiber glass as set forth in Table 2 was mixed with 50 wt % of polymethylmethacrylate (Type D), and the mixture was extruded to prepare an implant material (Diameter: 1.5 cm, Height: 10 cm) of the invention. 10 wt % of each of Run Nos. 4 and 5 of the fiber glass as set forth in Table 2 was mixed with 90 wt % of polymethylmethacrylate (Type D), the following procedures being similar to Example 1, to prepare a sample, and the bending strength and modulus of bending elasticity of each sample were measured. The results are shown in Table 3.

TABLE 3

| Fiber Glass Run No. | Bending Strength (kg/cm$^2$) | Modulus of Bending Elasticity (kg/cm$^2$) | Density (g/cm$^3$) |
|---|---|---|---|
| 2 | 2000 | 1.9 × 10$^5$ | 1.8 |
| 3 | 2000 | 1.9 × 10$^5$ | 1.8 |
| 4 | 500 | 0.6 × 10$^5$ | 1.3 |
| 5 | 500 | 0.6 × 10$^5$ | 1.3 |

All of the implant materials were tough and could be cut by a knife, and had portions of fiber glasses exposed on the surfaces thereof.

With each of the implant materials prepared from the fiber glasses produced in Run Nos. 2 to 5 an artificially formed defect (3 mm$\phi$ × 4 mmL) in a femur of a rabbit was filled, and the portion filled with each implant material was inspected after the lapse of twelve weeks. The results were that all of the implant materials were unified substantially integrally with the surrounding bone tissues.

EXAMPLE 4

The fiber glass produced by Run No. 2 in Example 3 was dipped in aqueous ammonia solutions, to which phosphoric acid had been added and having, respectively, a pH value of 1.0, 2.0, 4.0, 6.0, 7.0 and 8.0, to treat the surfaces of the fiber glasses for 30 minutes. The fibers treated at pH 1.0 were adversely attacked by the treating solution so as to have rugged surfaces. The fiber glasses treated at pH 8.0 had the surfaces which were scarcely covered with the deposition. The fiber glasses treated, respectively, at pH 2.0 to 7.0 were covered by the deposition, and particularly the surfaces of the fiber glasses treated at pH 4.0 and 6.0 were covered with the deposition uniformly.

An implant material was prepared from the fiber glass treated at pH 4.0, following procedures similar to those described in Example 3, and implanted in a defect in the femur of a rabbit similarly to Example 3. The growth of new bone was observed after the lapse of three weeks. The result was that the amount of growing new bone was larger than that observed in Example 3.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense.

The present invention is limited only by the scope of the following claims.

What is claimed is:

1. An implant material for replacing hard tissue of a living body, comprising 10 to 90% by weight of a fiber glass mainly composed of calcium phosphate and 90 to 10% by weight of an organic high polymer material not inhibiting affinity with the living body, the surface of the fiber glass being coated with a calcium phosphate compound having a Ca/P molar ratio of from 0.8 to 1.7 and resulting from dipping the fiber glass in a solution containing phosphoric ions and having a pH value of from 2 to 7, a portion of said fiber glass being exposed on the surface of said implant material, said implant material having a bending strength of from 500 kg/cm$^2$ to 16500 kg/cm$^2$, a modulus of bending elasticity of from 0.6 to 10$^5$ kg/cm$^2$ to 5.5 × 10$^5$ kg/cm$^2$, and a density of from 1.3 to 2.3 g/cm$^3$, said fiber glass containing a total content of CaO and P$_2$O$_5$ of not less than 15% by weight, and having a molar ratio of Ca/P of from 0.3 to 4.0, the bending strength, the modulus of bending elasticity and the density being adjusted within said range by varying the content of the fiber glass.

2. The implant material according to claim 1, wherein said fiber glass is prepared by melting and then cooling a starting material selected from the group consisting of a single calcium phosphate compound, a combination of a calcium phosphate compound with one or more of other phosphorous-containing compounds, a combination of a calcium phosphate compound with one or more of other calcium-containing compounds, and a combination of one or more of said other phosphorous-containing compounds with one or more of said other calcium-containing compounds.

3. The implant material according to claim 2, wherein said calcium phosphate compound is selected from the group consisting of tetracalcium phosphate, hydroxyapatite, tricalcium phosphate, animal bones and mixtures thereof.

4. The implant material according to claim 2, wherein said other calcium-containing compound is selected from the group consisting of quick lime, slaked lime, calcium carbonate and mixtures thereof.

5. The implant material according to claim 2, wherein said other phosphorous-containing compound is selected from the group consisting of triammonium phosphate, ammonium hydrogenphosphate, sodium phosphate, phosphoric acid and mixtures thereof.

6. The implant material according to claim 2, wherein said starting material further includes an inorganic oxide.

7. The implant material according to claim 6, wherein said inorganic oxide is selected from the group consisting of alumina, silica, sodium oxide, potassium oxide, iron oxide, magnesium oxide, potash feldspar, kaolin and mixtures thereof.

8. The implant material according to claim 1, wherein said solution containing phosphoric ions is selected from the group consisting of a solution of ammonium hydrogenphosphate and a mixed solution of phosphoric acid and ammonia.

9. The implant material according to claim 1, wherein said organic high polymer material is selected from the group consisting of a carboxylic acid base polymer, a carboxylic ester base polymer and an olefinic polymer.

10. The implant material according to claim 9, wherein said carboxylic acid base polymer is selected from the group consisting of polylactic acid and polyglycolic acid.

11. The implant material according to claim 9, wherein said carboxylic ester base polymer is selected from the group consisting of polymethylmethacrylate and poly(trifluoroethylmethacrylate).

12. The implant material according to claim 9, wherein said olefinic polymer is selected from the group consisting of polyethylene and polypropylene.

13. An implant material for replacing hard tissue of a living body, comprising 10 to 90% by weight of a fiber glass mainly composed of calcium phosphate and 90 to 10% by weight of an organic high polymer material not inhibiting affinity with the living body, the surface of the fiber glass being coated with a calcium phosphate compound having a Ca/P molar ratio of from 1.0 to 2.0 and resulting from dipping the fiber glass in a slurry of a calcium phosphate compound having a Ca/P ratio of from 1.0 to 2.0 and then drying the slurry on the fiber glass, a portion of said fiber glass being exposed on the surface of said implant material, said implant material having a bending strength of from 500 kg/cm$^2$ to 16500 kg/cm$^2$, a modulus of bending elasticity of from $0.6 \times 10^5$ kg/cm$^2$ to $5.5 \times 10^5$ kg/cm$^2$, and a density of from 1.3 to 2.3 g/cm$^3$, said fiber glass containing a total content of CaO and P$_2$O$_5$ of not less than 15% by weight, and having a molar ratio of Ca/P of from 0.3 to 4.0, the bending strength, the modulus of bending elasticity and the density being adjusted within said range by varying the content of the fiber glass.

14. The implant material according to claim 13, wherein said fiber glass is prepared by melting and then cooling a starting material selected from the group consisting of a single calcium phosphate compound, a combination of a calcium phosphate compound with one or more of other phosphorous-containing compounds, a combination of a calcium phosphate compound with one or more of other calcium-containing compounds, and a combination of one or more of said other phosphorous-containing compounds with one or more of said other calcium-containing compounds.

15. The implant material according to claim 14, wherein said calcium phosphate compound is selected from the group consisting of tetracalcium phosphate, hydroxyapatite, tricalcium phosphate, animal bones and mixtures thereof.

16. The implant material according to claim 14, wherein said other calcium-containing compound is selected from the group consisting of quick lime, slaked lime, calcium carbonate and mixtures thereof.

17. The implant material according to claim 14, wherein said other phosphorous-containing compound is selected from the group consisting of triammonium phosphate, ammonium hydrogenphosphate, sodium phosphate, phosphoric acid and mixtures thereof.

18. The implant material according to claim 14, wherein said starting material further includes an inorganic oxide.

19. The implant material according to claim 18, wherein said inorganic oxide is selected from the group consisting of alumina, silica, sodium oxide, potassium oxide, iron oxide, magnesium oxide, potash feldspar, kaolin and mixtures thereof.

20. The implant material according to claim 14, wherein said organic high polymer material is selected from the group consisting of a carboxylic acid base polymer, a carboxylic ester base polymer and a olefinic polymer.

21. The implant material according to claim 20, wherein said carboxylic acid base polymer is selected from the group consisting of polylactic acid and polyglycolic acid.

22. The implant material according to claim 20, wherein said carboxylic ester base polymer is selected from the group consisting of polymethylmethacrylate and poly(trifluoroethylmethacrylate).

23. The implant material according to claim 20, wherein said olefinic polymer is selected from the group consisting of polyethylene and polypropylene.

* * * * *